US005507818A

United States Patent [19]
McLaughlin

[11] Patent Number: 5,507,818
[45] Date of Patent: Apr. 16, 1996

[54] MULTIPOLAR JOINT ENDOPROSTHESIS

[76] Inventor: John A. McLaughlin, 15 Storehill Rd., Old Westbury, N.Y. 11568

[21] Appl. No.: 271,202

[22] Filed: Jun. 30, 1994

[51] Int. Cl.⁶ .................................. A61F 2/30; A61F 2/32
[52] U.S. Cl. ............................................. 623/18; 623/23
[58] Field of Search ............................ 623/16, 17, 18, 623/19, 20, 22, 23, 35, 36, 37

[56] References Cited

U.S. PATENT DOCUMENTS

| | | | |
|---|---|---|---|
| 3,414,908 | 12/1968 | Waggott et al. | 623/38 |
| 3,671,978 | 6/1972 | May | 623/23 |
| 4,563,898 | 8/1985 | Palfray | 623/38 |
| 4,923,472 | 5/1990 | Ugolini | 623/38 |
| 5,336,268 | 8/1994 | Rispeter | 623/23 |

FOREIGN PATENT DOCUMENTS

| | | | |
|---|---|---|---|
| 0549480 | 6/1993 | European Pat. Off. | 623/23 |
| 3535158 | 4/1987 | Germany | 623/23 |
| 3710233 | 10/1988 | Germany | 623/23 |

*Primary Examiner*—David Isabella
*Attorney, Agent, or Firm*—Dilworth & Barrese

[57] ABSTRACT

A multipolar joint endoprosthesis for joint replacement includes multiple wedge shaped, cylindrical components attached in sequence to proximal and distal components (designed to be affixed to bone) each inseparable except by surgical manipulation and each freely, passively rotating about axes perpendicular to its planes of effacement with adjacent components. This passive rotation of one or more of the wedge-shaped components alters the angular orientation of the proximal and distal components thereby allowing range of motion of the joint in question.

18 Claims, 4 Drawing Sheets

5,507,818

MULTIPOLAR JOINT ENDOPROSTHESIS

BACKGROUND OF INVENTION

Various joint endoprostheses have previously been proposed. While generally satisfactory for the purpose of orthopaedic joint replacement, they have been found unsatisfactory for a number of reasons: dislocation, dissociation of components, bony wear, acetabular protrusio, pain, polyethylene wear, limited range of motion, etc.

It is therefore an object of the present novel invention to provide a joint endoprosthesis which overcomes the disadvantages of prior systems as set forth above.

It is further an object of the present invention to be highly effective and reliable in its operation.

SUMMARY OF INVENTION

The multipolar joint endoprosthesis presented consists of multiple wedge-shaped, cylindrical components that are inseparable except by surgical manipulation, but rotate freely about an axis perpendicular to their planes of effacement with adjacent components. In addition to the components described, two additional components are included: (1) a component, herein known as the proximal component, contoured to fit the proximal side of the surgically prepared joint (i.e. the glenoid fossa of the gleno-humeral joint, the acetabulum of the hip, etc.) and (2) a component, herein known as the distal component, contoured to fit the distal side of the surgically prepared joint or into the surgically prepared intramedullary canal distal to the involved joint (i.e. intramedullary canal of the humerus, hip, etc.). The proximal and distal components similarly rotate about an axis perpendicular to their planes of effacement with the wedge shaped components. The proximal and distal components are also inseparable from the other components except by surgical manipulation. The proximal and distal components can be firmly affixed to their corresponding bony landmarks utilizing methylmethacrylate bone cement, screws, bony ingrowth, etc.

Since the planes of effacement of each wedge-shaped component are non-parallel and converging, passive rotation of one or more of the wedge-shaped components alters the angle of orientation between the proximal and distal components, thereby allowing for range of motion in all directions of the bony structures to which the proximal and distal components are attached.

Since there is no motion at the bone-prosthesis interfaces, it is hypothesized that many of the problems of previously proposed endoprostheses would be resolved (i.e. bony wear, acetabular protrusio, pain, etc.). In addition, the components are inseparable except by surgical manipulation, as noted above, avoiding the problems of dislocation, dissociation of components, etc. Finally, by allowing motion at multiple component interfaces, the problems of polyethylene/component wear and limited range of motion are eliminated.

BRIEF DESCRIPTION OF DRAWING

Other objects and features of the present invention will become apparent from the detailed description when studied in connection with the accompanying drawings which disclose several embodiments of the invention. It is to be understood that the drawings are designed for the purpose of illustration only and are not intended as a definition of the limits of the invention. For the purpose of illustration, the present invention is represented as a hip endoprosthesis. However, it is not meant to imply that the present invention is limited to use in the hip. Thus, while several embodiments of the present invention have been shown and described, it will be obvious that many changes and modifications may be made thereunto, without departing from the spirit or scope of the invention.

In the drawings, several reference characters denote similar elements throughout the several views.

DETAILED DESCRIPTION OF DRAWINGS

Figure 1:
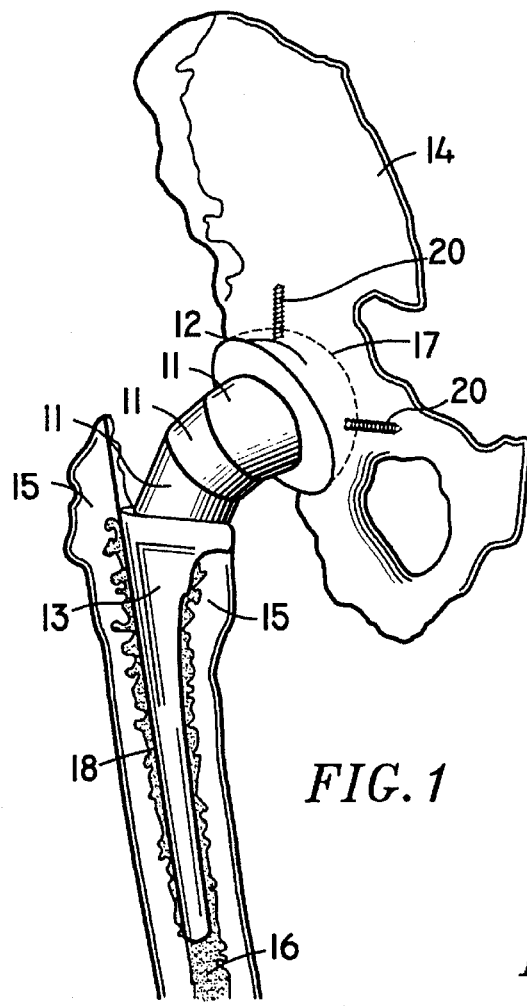
FIG. 1 is a frontal view of a joint endoprosthesis embodying the present invention functioning as a hip endoprosthesis. The figure illustrates the orientation of the various components with the lower extremity in the anatomic position (i.e. standing).
Figure 3:
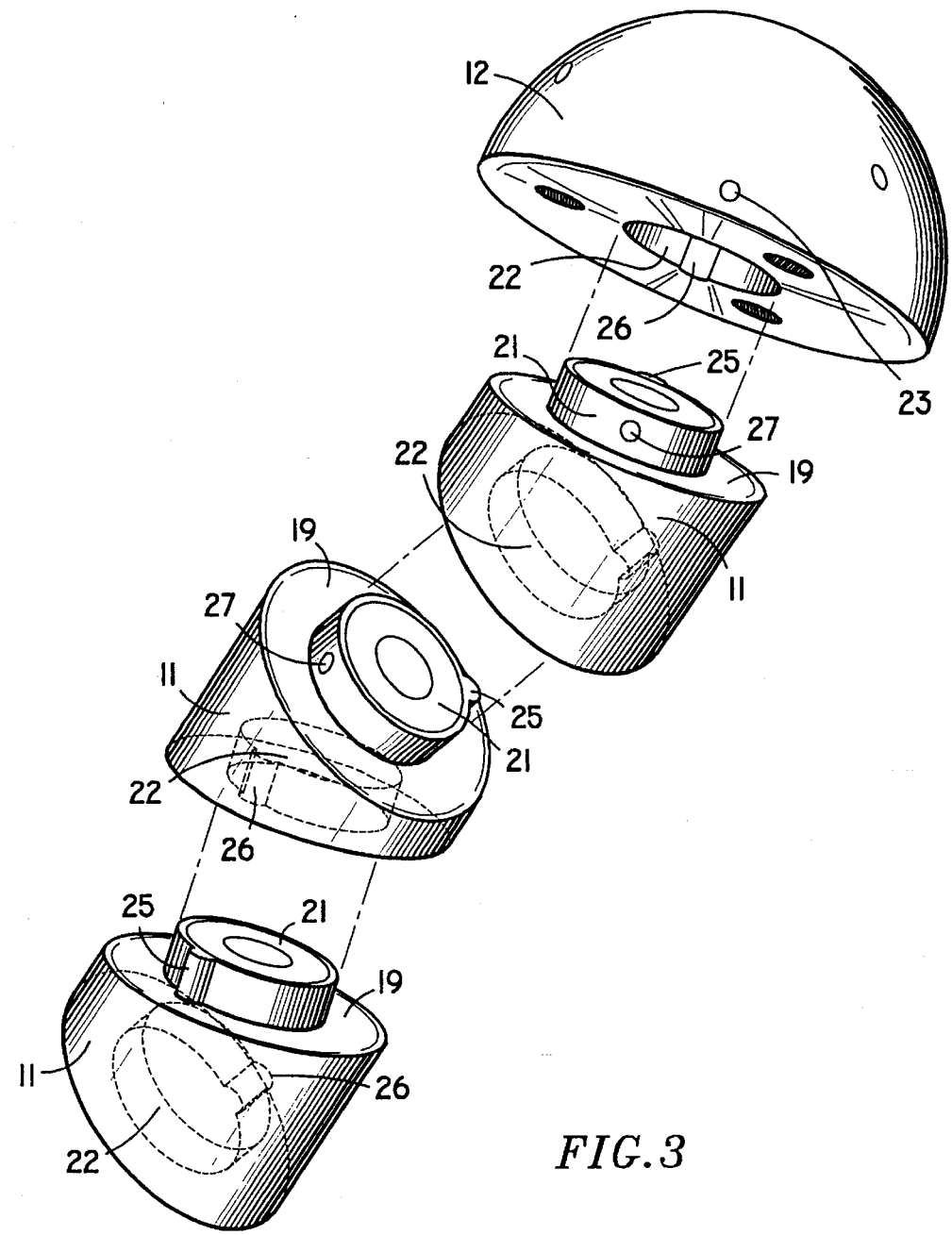
FIG. 3 is an exploded view of a joint endoprosthesis embodying the present invention illustrating one possible mechanism for its assembly.
Figure 4:
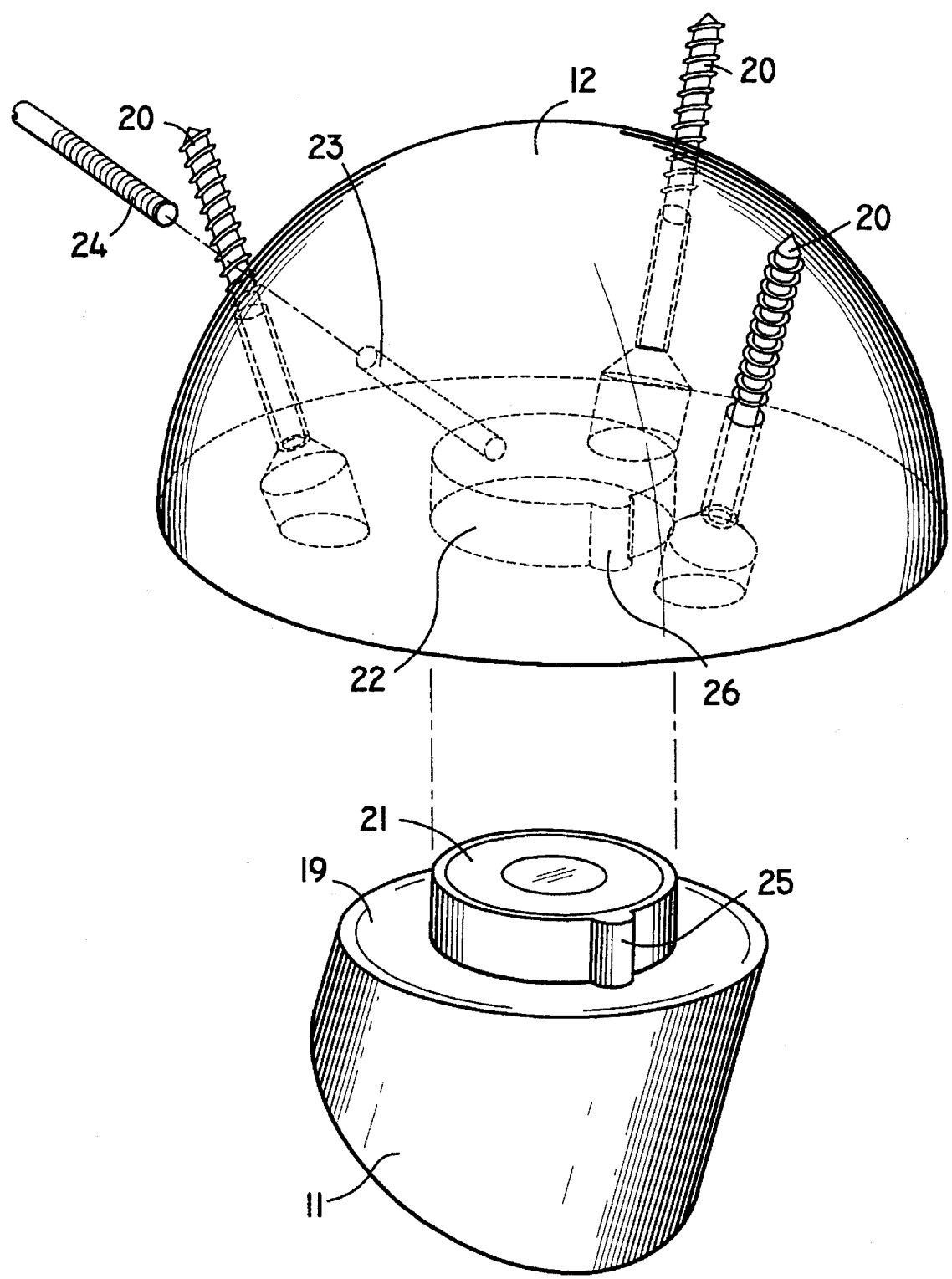
FIG. 4 is an exploded view of the component and its relationship to the first wedge-shaped component.
Figure 5:
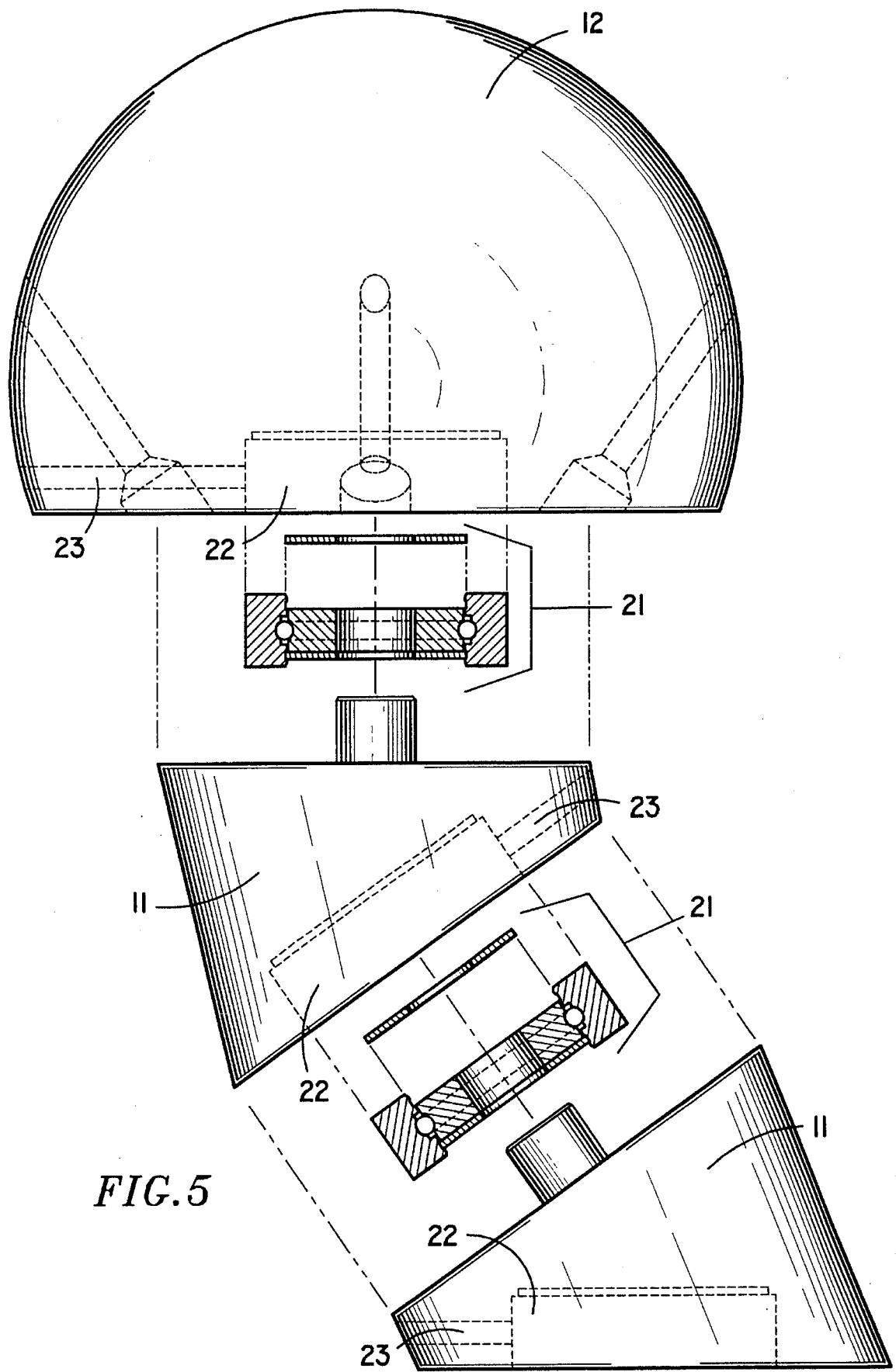
FIG. 5 is an exploded, planar view illustrating one possible swivel mechanism and mode of assembly.

Referring now in detail to the appended drawings, and in particular to FIG. 1 thereof, illustrated is a novel multipolar endoprosthesis embodying the present invention functioning, for the purposes of illustration, as a hip endoprosthesis. The proximal component 12 is firmly affixed to the proximal bony landmark (eg. pelvis) 14 by means of methylmethacrylate bone cement, screws 20, bony ingrowth, etc. in such a way that no motion occurs at the proximal component-bone interface 17. Attached to the proximal component 12 is the first of multiple wedge-shaped components 11 as illustrated in FIGS. 3 and 4. Variation on the assembly technique are possible without departing from the spirit and scope of the invention. The swivel 21, shown in FIG. 1 as a rotatable bearing, is firmly attached to the plane of effacement 19 of a wedge-shaped component 11 via a screw or weld, and is inserted into the swivel receptacle 22 of the proximal component 12 aligning the key 25 with the key hole 26. Aligning the key 25 and the key hole 26 (FIGS. 3 and 4) during insertion of the swivel 21 into the swivel receptacle 22 assures the alignment of the screw tract 23 and screw hole 27. Screwing the set screw 24 through the screw tract 23 and into the screw hole 27 prevents separation or dissociation of the components. Additional wedge-shaped components 11 and the distal component 13 are similarly attached. The distal component 13 is firmly affixed to the distal bony landmark (eg. femur) 15 or into the surgically prepared intramedullary canal 16 by means of methylmethacrylate bone cement, screws, bony ingrowth, etc. in such a way that no motion occurs at the distal component-bone interface 18. While the components 11,12,13 are inseparable except by surgical manipulation, each rotates around axes perpendicular to its planes of effacement 19. Variations on the swivel mechanism are possible without departing from the spirit and scope of the invention.

Passive rotation of one or more of the wedge-shaped components 11 about axes perpendicular to their planes of effacement 19 alters the angular orientation of the wedge-shaped components 11 and, therefore, the proximal component's 12 angular orientation to the distal component 13.

Figure 2A:
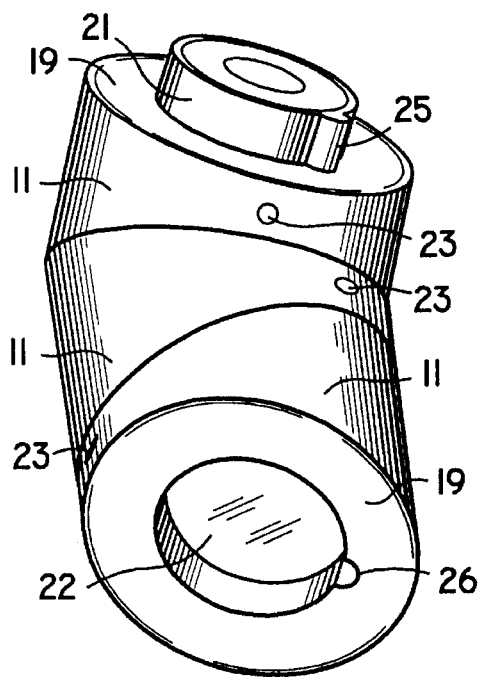
FIG. 2 (A and B) consists of two views of the assembled wedge-shaped components illustrating two different orientations. The proximal and distal components are not included to better illustrate the wedge-shaped components.
Figure 2B:
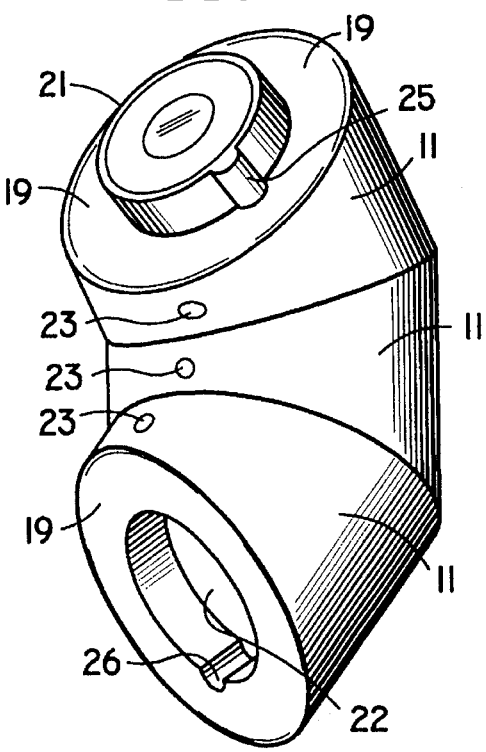

This, in turn, alters the angular orientation of the bones 14,15 to which the proximal component 12 and distal component 13 attach. Two different angular orientations are depicted in FIG. 2A and 2B. This illustration is not meant to imply that these are the only two angular orientations that can be assumed.

Thus, while only several embodiments of the present invention have been shown and described, it will be obvious that many changes and modifications may be made thereunto without departing from the spirit and scope of the invention.

What is claimed:

1. A joint endoprosthesis comprising:
   first and second anchoring components, each of said components including a mounting face having engaging structure;
   a plurality of obliquely truncated cylindrical members interconnecting said first and second anchoring components, each of said truncated cylindrical members including structure for interlocking with the engaging structure of said anchoring components and configured to permit continuous relative multiplanar movement of the anchoring components during use.

2. A joint endoprosthesis according to claim 1 wherein each of said truncated cylindrical members includes a first and a second mounting face, said interlocking structure being positioned on said mounting faces of said cylindrical members.

3. A joint endoprosthesis according to claim 1 wherein said engaging structure comprises a swivel member formed on one of said anchoring components and a swivel member receptor formed on the other of said anchoring components.

4. A joint endoprosthesis according to claim 3 wherein said swivel member includes a rotatable bearing.

5. A joint endoprosthesis according to claim 3 wherein each of said truncated cylindrical members include first and second mounting faces, said interlocking structure being positioned on said first and second mounting faces of said truncated cylindrical members, and wherein said interlocking structure comprises a swivel member positioned on one of said first and second mounting faces and a swivel member receptor formed on the other of said first and second mounting faces, wherein each of said swivel members of said engaging structure and said interlocking structure is configured to be received within a respective one of said swivel member receptors of said engaging and interlocking structure to permit said relative multiplanar movement of the anchoring components.

6. A joint endoprosthesis according to claim 2 wherein said first mounting face of each of said truncated cylindrical members is angled with respect to the second mounting face of said truncated cylindrical member.

7. A joint endoprosthesis according to claim 6 wherein said plurality of truncated cylindrical members include at least three truncated cylindrical members.

8. A joint endoprosthesis according to claim 5 further comprising a retaining means for retaining each of said swivel members within said respective swivel member receptor.

9. A joint endoprosthesis comprising:
   a first anchoring component configured to be affixed within a body joint and having a swivel receptor formed therein;
   a second anchoring component configured to be affixed to a bone and having a swivel positioned thereon;
   first, second and third obliquely truncated cylindrical members positioned between said first and second anchoring components, each of said members having a first mounting face having a swivel member positioned thereon and a second mounting face having a swivel member receptor formed therein;
   wherein the swivel member positioned on said first truncated cylindrical member is configured to engage the swivel member receptor formed in said first anchoring component, the swivel member positioned on said second truncated cylindrical member is configured to engage the swivel member receptor formed in the first truncated cylindrical member, the swivel member positioned on the third truncated cylindrical member is configured to engage the swivel member receptor formed in the second truncated cylindrical member, and the swivel member positioned on the second anchoring component is configured to engage the swivel member receptor formed in the third truncated cylindrical member, such as to permit continuous relative multiplanar movement of the anchoring components during use.

10. A joint endoprosthesis according to claim 9 further comprising means for retaining each of said swivel members in engagement with its respective swivel member receptor.

11. A joint endoprosthesis according to claim 9 wherein said first mounting face is angled with respect to said second mounting face.

12. A joint endoprosthesis according to claim 9 wherein each of said swivel members include a rotatable bearing.

13. A joint endoprosthesis comprising:
   first and second anchoring components, each of said components having engaging structure;
   a plurality of obliquely truncated cylindrical members interconnecting said first and second anchoring components, each of said truncated cylindrical members being rotatably connected to at least one adjacent truncated cylindrical member, one of said truncated cylindrical members being connected to said engaging structure of said first anchoring component and another of said truncated members being connected to said engaging structure of said second anchoring component to thereby permit continuous relative multiplanar movement of said anchoring components during use.

14. A joint endoprosthesis according to claim 13 wherein said plurality of truncated cylindrical members comprise at least three truncated cylindrical members.

15. A joint endoprosthesis according to claim 13 wherein each of said truncated cylindrical members comprise a pair of mounting faces, wherein one of said mounting faces of each of said truncated cylindrical members rotatably engages one of the mounting faces of each adjacent truncated cylindrical members.

16. A joint endoprosthesis according to claim 15 wherein the engaged mounting faces of the adjacent truncated cylindrical members have different angular orientations.

17. A joint endoprosthesis according to claim 16 wherein said plurality of truncated cylindrical members comprise at least three truncated cylindrical members.

18. A joint endoprosthesis according to claim 13 further comprising a rotatable bearing rotatably connecting each of said truncated cylindrical members to said at least one adjacent cylindrical member.

* * * * *